United States Patent [19]

Luedicke, Jr. et al.

[11] 4,144,326
[45] Mar. 13, 1979

[54] OIL FREE, WATER-SOLUBLE, CLEAR CREME RINSE FOR HAIR

[75] Inventors: Oscar B. Luedicke, Jr., Butler; Francis M. Gichia, Paterson, both of N.J.

[73] Assignee: American Cyanamid Company, Stamford, Conn.

[21] Appl. No.: 770,874

[22] Filed: Feb. 22, 1977

Related U.S. Application Data

[63] Continuation of Ser. No. 578,438, May 19, 1975, abandoned.

[51] Int. Cl.$^2$ ............................................. A61K 7/08
[52] U.S. Cl. .............................. 424/70; 424/DIG. 2; 424/78; 424/362
[58] Field of Search ................... 424/70, DIG. 2, 78, 424/362

[56] References Cited

U.S. PATENT DOCUMENTS 3,822,312  7/1974  Sato et al. ............................... 424/70
3,876,760  4/1975  Nersesian et al. ...................... 424/70

FOREIGN PATENT DOCUMENTS 727,588    2/1966   Canada ....................................... 424/70
1,402,017  3/1965   France ....................................... 424/70
1,209,560  10/1970  United Kingdom ....................... 424/70

OTHER PUBLICATIONS

Lehne, American Perfumer & Cosmetics, vol. 78, No. 10, Oct. 1963, pp. 103–107.
Shansky, American Perfumer & Costmetics, vol. 80, No. 2, Feb. 1965, pp. 33–35.

*Primary Examiner*—Albert T. Meyers
*Assistant Examiner*—Vera C. Clarke
*Attorney, Agent, or Firm*—Charles J. Fickey

[57] ABSTRACT

An aqueous creme rinse composition is provided comprising water and from about 0.25 to 5.0 parts by weight of lauryl trimethyl ammonium chloride or bromide, 0.25 to 3.0 parts of dimethyl dialkyl ammonium chloride or bromide and a quaternized hydroxymethyl cellulose.

2 Claims, No Drawings

OIL FREE, WATER-SOLUBLE, CLEAR CREME RINSE FOR HAIR

This is a continuation of application Ser. No. 578,438, filed May 19, 1975 now abandoned.

Generally stated, the subject matter of the present invention relates to a new creme rinse formulation for hair. More particularly, the invention relates to a new creme rinse formulation which is a substantially clear, oilfree product which is water soluble and which on dilution with water results in a substantially clear aqueous composition.

BACKGROUND OF THE INVENTION

Creme rinse compositions are normally used to condition or improve hair subsequent to shampooing. Although various shampoo compositions have been devised to result in an improved condition of the hair after shampooing so as to minimize the necessity for subsequent creme rinse treatment, there remains a substantial need for creme rinse compositions since the so-called conditioning shampoos fail to completely achieve the desired results.

The effective cleansing action of shampoos results in the removal, to a large degree, of the naturally occurring oils and surface components of the hair so that after drying, the hair is left in a condition where it is dull and raspy and may retain static electric charges causing the hair to fly away with snarling and tangles making it difficult to comb and becoming generally unmanageable. This has prompted the evolution of the creme rinse compositions which are applied to the hair after shampooing to impart luster and manageability to the hair.

In the past, long chain alkyl containing quaternary ammonium compounds have been used in creme rinse formulations to achieve the improved condition of the hair. A quaternary ammonium compound of this type which has had particular application in such formulations is stearyl dimethylbenzyl ammonium chloride. In addition, other types of oil or fatty materials have been incorporated in shampoos and rinses to achieve an improved condition of the hair, including for example, small amounts of mineral oil, lanolin, protein products, fatty alcohols, nonionic surfactants, and the like.

In general, the available creme rinse formulations appear as cloudy, pearlescent, or opaque mixtures to convey the concept of creaming, which on further dilution with water results in cloudy appearing compositions. In some instances, there is a separation of an oil phase. Moreover, while the beneficial effects of a creme rinse are very desirable, e.g., the hair is easier to comb, has gloss, and has no fly-away effect, there are also undesirable effects from the use of creme rinses. For example, the available creme rinses containing oily or fatty components emulsions, i.e., suspensions of oil in water, and are not soluble in water. Webster's New Collegiate Dictionary, Eighth Edition, defines an oil as .... "any of numerous unctuous combustible substances that are liquid or at least easily liquifiable on warming, are soluble in ether but not in water, and leave a greasy stain on paper or cloth." Thus, due to the nature of oils, creme rinses containing them are not solubilized and are not completely removed from the hair. An oily coating remains on the hair. Consumers have complained of an undesirable feeling of fullness of the hair and a certain amount of greasiness. In addition, the oil attracts dirt which makes it necessary to wash the hair more often, from twice a week to daily. This however increases the difficulties of washing (split-ends, frizziness, fly-away, tangles) for which the creme rinse must be used, however, bringing back the unwelcome feeling of oiliness and dirt which washing was intended to remove. We have found that some consumers would prefer to use a creme rinse which does not have the oily effects, and yet for obvious reasons it would function as a creme rinse to give the desired hair manageability. Accordingly, notwithstanding an enormous effort, it was only in the most unexpected way that we found a creme rinse which was water white, oil free, water soluble and possessed excellent rinsing qualities to achieve the desired manageability effects without the undesirable oil effects. In the course of our investigation of numerous surface active agents, some had this water white quality but lacked in creme rinse properties and vice versa.

It is, therefore, a primary object of the invention to provide a new and improved creme rinse formulation which has no oil components and which conditions the hair without imparting an oily feeling or appearance to the hair, and does not attract dirt.

Another object of this invention is to provide a water white creme rinse formulation which is clear and transparent, water soluble, and which on further dilution with water retains a clear appearance without development of a haze or a separation of phases.

Still another object of this invention is to provide a new and improved water white creme rinse formulation which on application to the hair results in good foamability and imparts to the hair a desirable conditioning effect.

Additional objects and advantages will be set forth in part in the description which follows, and in part will be obvious from the description, or may be learned by practice of the invention, the objects and advantages being realized and attained by means of the compositions, processes and improvements particularly pointed out in the appended claims.

The present invention is a new oil free, water soluble, water white creme rinse composition wherein the primary conditioning agent is a quaternary ammonium compound of relatively low molecular weight with shorter alkyl chain than normally occurs, specifically it is lauryl trimethylammonium chloride or bromide. These compounds can be used in combination with other lower molecular weight quaternaries which markedly improve the clarity of the creme rinse and its rinsing properties. The second quaternary can be dialkyl dimethyl quaternary ammonium chloride or bromide in which the dialkyl group is a mixture of $C_{12}$–$C_{18}$ branched and straight chain moieties.

The creme rinse compositions of the invention with the lauryl trimethyl-ammonium chloride compound in combination with dialkyl dimethyl quaternary ammonium chloride on application result in good water white creme rinse conditioning action with no oily feel; and on further dilution of the composition with water there is no haze or cloudy appearance, and naturally no oil separation. The pH of the compositions is generally maintained in the range of about 2.5 to 7, preferably at about 3.5 to 5.5. The pH range may be adjusted to or maintained at the desired figure by the addition, if necessary, of mildly acidic agents as generally used in hair formulations, for example, by the addition of citric acid, and the like.

Although it has been known to use various quaternary compounds in creme rinses, the use of the lauryl trimethyl-ammonium compound in combination with dialkyl dimethyl quaternary ammonium compound affords a composition containing no oily active ingredients, satisfying the requirements for a clear, non-cloudy or hazy formulation which even on dilution with water actual use has good foamability but remains clear, i.e., water white, with no separation of an oily phase or development of a cloudy or hazy appearance.

In the composition of the invention from about 0.25 parts to 5.0 parts, preferably 1 to 4 of the lauryl trimethyl ammonium compounds or in combination with 0.25 parts to 3.0 parts dialkyl dimethyl quaternary ammonium compounds and/or 0.2 parts as real solids are used per 100 parts of the composition with a preferred range of about 0.75 parts to 9.0 parts. Normally an antifreeze agent is included to the extent of about 3 parts to 14 parts of the composition, preferably between about 4 and 11 parts. Accordingly, the antifreeze agent is one that is acceptable for cosmetic usage and therefore a "cosmetic antifreeze agent" is intended for the purpose of this specification to mean such an anitfreeze agent, and solvents such as propylene glycol, isopropanol or ethanol are particularly suitable for this purpose.

As stated above the pH of the composition desired may be adjusted to 2.5 to 7, preferably about 5 by the addition of a mildly acidic material such as citric acid, tartaric acid, phosphoric acid, lactic acid, and the like. For the purpose of this specification, mildly acidic materials such as those herein recited, which are acceptable for cosmetic usage, shall be referred to as "a cosmetic acid".

In addition, various other additives conventionally used in creme rinses or other hair conditioning products are included in minor amounts such as thickeners, e.g., a quaternized hydroxymethyl cellulose, preservatives, stabilizers, colorants, perfume, etc.

Thus, as stated above, these new compositions contain no oily active ingredients and remain clear even on dilution, and on application by conventional means give an improved conditioning effect to the hair.

The invention is further illustrated by the examples which follow:

EXAMPLE 1

The following components are combined to form a creme rinse composition:

| | Parts (%) |
|---|---|
| Isopropanol | 10.0 |
| Dodecyltrimethyl ammonium chloride (1) | 2.0 |
| Hydroxypropylmethylcellulose (2) | 0.15 |
| 90% Ethanol | 0.347 |
| Citric Acid | 0.2 |
| Ultraviolet Stabilizer (3) | 0.08 |
| Preservatives (4) | 0.2 |
| Colorant (as desired) | 0.005 |
| Perfume (as desired) | 0.6 |
| Water | to make 100 parts |

(1) Arquad 12-50 Surfactant*
(2) Methocel 60 HG 4000 Thickner
(3) 2,2',4,4'-tetrahydroxybenzophenone, Uvinol D-50
(4) 0.1% formalin and 0.1% Dowicil 200 (cis-isomer of 1-(3-chloroallyl)-2,5,7-triaza-1-azonia-adamantane chloride

*N-alkyl trimethylammonium chloride, normally available as a 50% solution. Thus, the amount of solids real is 1% of the quaternary.

The above components result in a clear solution which on further dilution with water remains clear and non-hazy and with no phase separation.

The creme rinse formulation of the Example may be applied to the hair by conventional procedures subsequent to the normal type of shampoo operation giving a desired conditioning effect.

EXAMPLE II

A creme rinse formulation is prepared according to the procedure of Example I, except that 10 parts of propylene glycol were used in place of the 10.0 parts of isopropanol, and 0.25 parts of hydroxypropylmethylcellulose are used instead of 0.15 parts.

The above components result in a clear solution which on further dilution with water remains clear and non-hazy and with no phase separation.

The creme rinse formulation of this Example may be applied to the hair by conventional procedures subsequent to the normal type of shampoo operation giving a desired conditioning effect.

EXAMPLE III

The following components are combined to form a creme rinse composition:

| | Parts (%) |
|---|---|
| Ethanol | 5.700 |
| Dodecyltrimethyl ammonium chloride (1) | 8.000 |
| Cellulose quaternarized polymer (2) | .500 |
| Dimethyl dialkyl ammonium chloride (3) | 4.000 |
| Ultraviolet stabilizer (4) | .080 |
| Preservatives (5) | .100 |
| Colorant (as desired) | .003 |
| Perfume (as desired) | .150 |
| Water | to make 100 parts |

(1) Arquad 12-50 Surfactant
(2) Polymer JR 30M (quaternized hydroxymethyl-cellulose)
(3) Adogen 432CG Surfactant*
(4) 2,2', 4,4'-tetrhydroxybenzophenone, Uvinol D-50
(5) 0.1% Formalin Normally available as a 75% solution. Thus, the amount of solids real is 7% of the quaternary. The dialkyl groups consist of:

1. 45% of equal amounts of straight chain $C_{12}$, $C_{13}$, $C_{14}$ and $C_{15}$
2. 15% of equal amounts of branched $C_{12}$, $C_{13}$, $C_{14}$ and $C_{15}$
3. 24.8% of straight chain $C_{16}$
4. 13.2% of straight chain $C_{13}$
5. 2% of straight chain $C_{14}$ sold as Adogen 432 CG.

The above components result in a clear solution which on further dilution with water remains clear and nonhazy and with no phase separation.

The creme rinse formulation of the Example may be applied to the hair by conventional procedures subsequent to the normal type of shampoo operation giving a desired conditioning effect.

EXAMPLE IV

The following components are combined to form a creme rinse composition:

| | Parts (%) |
|---|---|
| Ethanol | 5.000 |
| Dodecyltrimethyl ammonium chloride (1) | 6.000 |
| Cellulosic quaternarized polymer (2) | 0.500 |
| Dimethyl dialkyl ammonium chloride (3) | 2.000 |
| Perfume (as desired) | 0.150 |

| | Parts (%) |
|---|---|
| Water | to make 100 parts |

(1) Arquad 12-50 Surfactant *
(2) Polymer JR 30M and Polymer JR 400 (2:3)
(3) Adogen 432 CG Surfactant **
(4) 2, 2', 4, 4'-tetrahydroxybenzophenone, Uvinol D-50
(5) 0.1% Formalin (formaldehyde solution 38% sol.)

*Normally available as a 50% solution. **Normally available as a 75% solution. Thus, the amount of solids real is 7% of the quaternary.

The above components result in a clear solution which on further dilution with water remains clear and non-hazy and with no phase separation.

The creme rinse formulation of the Example may be applied to the hair by conventional procedures subsequent to the normal type of shampoo operation giving desired conditioning effect.

EXAMPLE V

The following components are combined to form a creme rinse composition:

| | Parts (%) |
|---|---|
| Ethanol | 5.000 |
| Dodecyltrimethyl ammonium chloride (1) | 8.000 |
| Cellulosic quaternarized polymer (2) | 0.500 |
| Dimethyl dialkyl ammonium chloride (3) | 4.000 |
| Preservatives (4) | 0.100 |
| Water | to make 100 parts |

(1) Arquad 12-50 Surfactant*
(2) Polymer JR 30M
(3) Adogen 432 CG Surfactant**
(4) 0.1% Formalin

*Normally available as a 50% solution. **Normally available as a 75% solution. Thus, the amount of solids real is 7% of the quaternary.

The above components result in a clear solution which no further dilution with water remains clear and nonhazy with no phase separation.

The creme rinse formulation of the Example may be applied to the hair by conventional procedures subsequent to the normal type of shampoo operation giving a desired conditioning effect.

We claim:

1. An aqueous water white creme rinse composition for improving the condition of the hair subsequent to a shampoo operation wherein the conditioning agent consists essentially of from 0.5% to 10% of lauryl trimethyl ammonium chloride or bromide, with from 0.25 to 5% dialkyl dimethyl quaternary ammonium chloride or bromide, said dialkyl groups having from about 12 to 18 carbon atoms.

2. The composition of claim 1 comprising in addition a quaternized cellulose ether.

* * * * *